United States Patent [19]

Yamanaka et al.

[11] Patent Number: 4,458,016

[45] Date of Patent: Jul. 3, 1984

[54] PRODUCTION OF 1-β-D-RIBOFURANOSYL-1,2,4-TRIAZOLE

[75] Inventors: Shigeru Yamanaka, Yokohama; Takashi Utagawa, Kawasaki; Tadad Kobayachi, Yokohama, all of Japan

[73] Assignee: Ajinomoto Co., Inc., Tokyo, Japan

[21] Appl. No.: 356,405

[22] Filed: Mar. 9, 1982

[30] Foreign Application Priority Data

Mar. 9, 1981 [JP] Japan ................................. 56-33304

[51] Int. Cl.³ .................... C12P 19/28; C12P 17/16; C12P 17/10; C12P 17/04
[52] U.S. Cl. .................................... 435/85; 435/118; 435/121; 435/123; 435/126; 435/147; 435/155
[58] Field of Search .................. 435/84, 85, 118, 121, 435/120, 123, 126, 147, 155; 536/23

[56] References Cited

U.S. PATENT DOCUMENTS 3,798,209  3/1974  Witkowski et al. ............... 536/23
3,856,777  12/1974 Ishido et al. ...................... 536/23
3,935,071  1/1976  Bergmeyer et al. ............... 435/137
3,976,545  8/1976  Witkowski et al. ............... 435/85
4,332,895  6/1982  Griffiths et al. ................ 435/207 X Primary Examiner—David M. Naff
Attorney, Agent, or Firm—Oblon, Fisher, Spivak, McClelland & Maier

[57] ABSTRACT

The production of a 1-β-D-ribofuranosyl-1,2,4-triazole of the formula

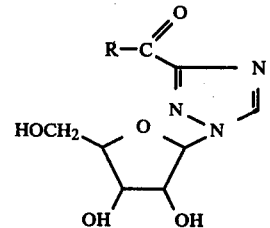

wherein R is hydroxy, amino, or alkoxy, is carried out by reacting a 1,2,4 triazole of formula

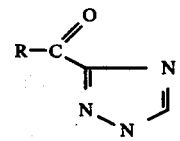

wherein R is hydroxy, amino, or alkoxy group, with a greater than equimolar amount of a ribofuranosyl group donor in the presence of a nucleoside phosphorylase preparation at a temperature in the range from 40° to 65° C. for more than 10 minutes, and recovering a 1-β-D-ribofuranosyl-1,2,4-triazole from the reaction solution. The temperature is preferably from 55° to 65° C. and the time is preferably 10 minutes to 20 hours. An elevated temperature higher than the usual enzyme reaction temperature isused to prevent undesirable enzymatic reactions.

4 Claims, No Drawings

PRODUCTION OF 1-β-D-RIBOFURANOSYL-1,2,4-TRIAZOLE

BACKGROUND OF THE INVENTION

1. Field of the Invention

The present invention relates to a method for producing 1-β-D-ribofuranosyl-1,2,4-triazoles of the formula

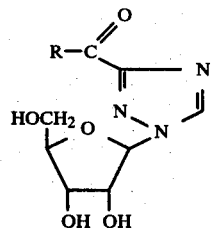

(I)

wherein R represents a hydroxy, amino, or alkoxy group, by an enzymatic process.

2. Description of the Prior Art

1-β-D-ribofuranosyl-1,2,4-triazoles of formula (I), especially 1-β-D-ribofuranosyl-1,2,4-triazole-3-carboxamide, which is commonly known as Virazole, are valuable compounds used as broad-spectrum antiviral agents (Chem. & Eng. News, 50, 26, Apr. 17, 1972).

1-β-D-Ribofuranosyl-1,2,4-triazoles may be produced by conventional synthetic methods, such as a method described in Witkowsky et al., 164th Am. Chem. Soc. Meeting, Boston, April, 1972. However, the known synthetic methods involve complex chemical processes and sometimes result in decreased yield as a result of by-product formation.

On the other hand, a fermentation process for the production of these triazole derivatives is known and is described in Japanese Published Examined Patent Application No. 17830/1979. This fermentation process comprises aerobically culturing bacteria of the genera Brevibacterium, Cornyebacterium, Arthrobacter, or Bacillus in a culture medium containing a 1,2,4-triazole of formula (II)

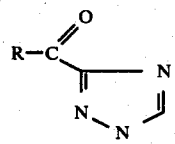

(II)

wherein R is a hydroxy, amino, or alkoxy group, for 2 to 8 days and recovering accumulated 1-β-D-ribofuranosyl-1,2,4-triazole from the culture broth. However, this fermentation process requires a long period of fermentation and complicated recovering steps to obtain purified product from the culture broth, which contains large amounts of various kinds of impurities.

SUMMARY OF THE INVENTION

Accordingly, it is an object of the present invention to provide an efficient process for producing 1-β-D-ribofuranosyl-1,2,4-triazoles by an enzymatic process.

This and other objects of the invention as will hereinafter become more readily apparent have been attained by providing a method for producing a 1-β-D-ribofuranosyl-1,2,4-triazole of the formula

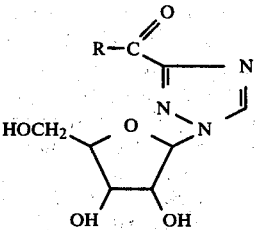

wherein R is a hydroxy, amino, or alkoxy group which comprises reacting a 1,2,4-triazole of the formula

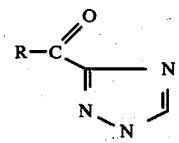

wherein R is as previously defined with a greater than equimolar amount of a ribofuranosyl group donor in the presence of a nucleoside phosphorylase preparation at a temperature in the range from 40° to 65° C. for more than 10 minutes, and recovering said 1-β-D-ribofuranosyl-1,2,4-triazole from the reaction solution.

DESCRIPTION OF THE PREFERRED EMBODIMENTS

According to the present invention, there is provided a method for producing 1-β-D-ribofuranoxyl-1,2,4-triazoles which comprises reacting a 1,2,4-triazole of formula (II) with a greater than equimolar amount of a ribofuranosyl group donor in the presence of a nucleoside phosphorylase preparation at a temperature in the range from 40° to 65° C. for more than 10 minutes and recovering a corresponding 1-β-D-ribofuranosyl-1,2,4-triazole of formula (I) from the reaction solution.

According to the method of the present invention, a 1-β-D-ribofuranosyl-1,2,4-triazole of formula (I) can be produced in accordance with any of the following three reactions:

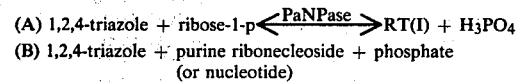
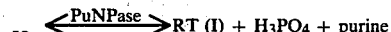
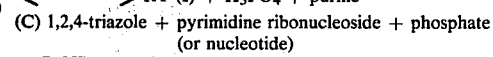
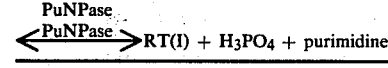

(A) 1,2,4-triazole + ribose-1-p $\xrightarrow{\text{PaNPase}}$ RT(I) + H$_3$PO$_4$ (B) 1,2,4-triazole + purine ribonecleoside + phosphate (or nucleotide)
$\xrightarrow{\text{PuNPase}}$ RT (I) + H$_3$PO$_4$ + purine (C) 1,2,4-triazole + pyrimidine ribonucleoside + phosphate (or nucleotide)
PuNPase
$\xrightarrow{\text{PuNPase}}$ RT(I) + H$_3$PO$_4$ + purimidine PuNPase: purine nucleoside phosphorylase
PyNPase: pyrimidine nucleoside phosphorylase
RT(I): a 1-β-D-ribofuranosyl-1,2,4-triazole of formula (I).

Nucleoside phosphorylases are well-known enzymes which catalyze phospholysis of nucleosides, thereby converting them into ribose-1-phosphate and a purine or pyrimidine. It is also known that purine arabinosides are produced by these enzymes from arabinose donors such as uracil arabinoside and other purine-sources such as adenine as is described in U.S. Pat. No. 3,856,777 and Japanese Published Examined Patent Application No. 36758/1976. However, it was not known prior to the present invention that these enzymes would catalyze reaction (A), (B), or (C).

It has now been found that reactions (A), (B), and (C) can all be catalyzed by nucleoside phosphorylases, and thereby a 1-β-D-ribofuranosyl-1,2,4-triazole of formula (I) can be produced efficiently from a triazole compound and a ribofuranosyl group donor.

Ribofuranosyl group donors suitable for the present invention include ribose-1-phosphate; purine nucleosides, such as adenosine, guanosine, xanthosine, and inosine; and pyrimidine nucleosides, such as uridine, thymidine, and cytosine. Additionally, purine nucleotides or pyrimidine nucleotides, such as adenylic acid, guanylic acid, inosinic acid, uridylic acid, and cytidylic acid, may also be used as ribofuranosyl group donors.

Nucleoside phosphorylases suitable for the present invention include purine nucleoside phosphorylases (EC 2.4.2.1) and pyrimidine nucleoside phosphorylases, such as uridine phosphorylase (EC 2.4.2.3) and thymidine phosphorylase (EC 2.4.2.4). A purine phosphorylase can catalyze reaction (A) and also catalyze reaction (B) when a purine nucleoside or purine nucleotide is used as the ribofuranosyl group donor and phosphate is additionally present. When a pyrimidine nucleoside or pyrimidine nucleotide is used as a ribofuranosyl group donor, both a pyrimidine nucleoside phosphorylase and a purine nucleoside phosphorylase must be present in order eto catalyze reaction (C).

The enzymes which catalyze reactions (A)–(C) occur in many different microorganisms. These include microorganisms belonging, as known so far, to to the genera Pseudomonus, Flavobacterium, Achromobacter, Salmonella, Erwinia, Bacterium, Citrobacter, Mycoplana, Escherichia, Enterobacter, Serratia, Klebsiella, Micrococcus, Xanthomonus, Corynebacterium, Bacillus, Cellulomonas, Arthrobacter, Brevibacterium, Sporosarcina, Aeromonus, Alcaligenes, Cadida, Sacchromyces, Staphylococcus, Kurthia, and Vibrio.

Specific examples of microorganisms from which the desired enzymes can be isolated include the following:

| Microorganism | Depository Identification |
| --- | --- |
| *Pseudomonas diminuta* | ATCC 11568 |
| *Favobacterium rhenanum* | CCM 298 |
| *Achromobacter lectium* | CCM 69 |
| *Salmonella schottmuelleri* | ATCC 8759 |
| *Erwinia herbicola* | ATCC 14536 |
| *Bacterium cadaveris* | ATCC 9660 |
| *Citrobacter freundii* | ATCC 8090 |
| *Mycoplana dimorpha* | ATCC 4279 |
| *Escherichia coli* | ATCC 10798 |
| *Enterobacter cloacae* | ATCC 13047 |
| *Serratia marcescens* | IFO 3046 |
| *Klebsiella pneumoniae* | ATCC 9621 |
| *Micrococcus luteus* | ATCC 398 |
| *Corynebacterium michiganense* | ATCC 7429 |
| *Bacillus brevis* | ATCC 8185 |
| *Cellulomonas flavigera* | ATCC 8183 |
| *Arthrobacter globitormis* | ATCC 8010 |
| *Bervibacterium ammoniagenes* | ATCC 6871 |
| *Alcaligenes metalcaligenes* | ATCC 13270 |
| *Sporosarcina ureae* | ATCC 6473 |
| *Aeromonas salmonicida* | ATCC 14174 |
| *Candida tropicalis* | ATCC 14056 |
| *Saccharomyces cerevisiae* | ATCC 2601 |
| *Staphylococcus epidermidis* | ATCC 155 |
| *Kurthia zophii* | ATCC 6900 |
| *Vibrio metchnikovii* | ATCC 7708 |

In order to produce the enzyme using a microorganism, such as those mentioned above, the microorganism is cultured in a conventional culture medium containing a carbon source, nitrogen source, inorganic ions, and, when required, minor organic nutrients such as vitamins and amino acids. Many culture media are suitable, and suitability of a particular medium for a particular strain can be determined by reference to many standard references, for example, *Catalogue of Stains I*, 15th ed., 1982, published by American Type Culture Collection, Rockville, Md., which is herein incorporated by reference. Cultivation of the microorganisms is carried out according to any conventional manner for that organism and medium. For example the microorganisms may typically be cultured aerobically at a pH ranging from 4.0 to 9.0 and at a temperature of from 25° to 40° C. Various preparations obtained from such cell cultures may be used to provide the enzymes catalyzing the phosphorylase reactions (A)–(C), for example, culture broth, intact cells, cells dried with acetone, freeze-dried or homogenized cells, sonicated cells, and cells treated with toluene or a lytic enzyme. By enzyme (or phosphorylase) preparation is meant any solution or suspension containing active nucleoside phosphorylase enzyme. Crude or purified enzyme obtained from disrupted cells is preferable used as the nucleoside phosphorylase preparation. Enzyme may be purified by any standard technique which separates proteins according to their physical and/or chemical properties, such as differential ammonium sulfate precipitation, gel filtration chromatography, or affinity chromatography. Fractions containing phosphorylase enzymes are easily determined using an enzymatic assay for phosphorylase activity or by using any one of reactions (A)–(C) described above in an enzymatic assay. Such enzyme purification is within the ability of those of ordinary skill in the art of enzyme purification.

A typical reaction mixture of the invention contains a 1,2,4-triazole of formula (II), a ribofuranosyl group donor in an amount greater than an equimolar amount of the triazole, and an enzyme preparation having nucleoside phosphorylase activity of from 0.01 to 5.0 units per milliliter in an aqueous solution. A "unit" of enzyme activity, here and elsewhere in this application, refers to the standard International Unit as defined for the particular enzyme activity being cited. When a nucleoside or nucleotide is used as the ribofuranosyl group donor, it is necessary to add phosphate to the reaction mixture. Phosphate acts as a catalyst in that it is used up in the conversion of the nucleoside or nucleotide into a purine or pyrimidine and ribose-1-phosphate but is generated again when the ribose-1-p reacts with the triazole to produce RT(I). Accordingly, the amount of phosphate added is not critical.

The enzyme reaction is carried out at a temperature ranging from 40° to 65° C. for from 10 minutes to 20 hours. It is critical that the enzyme reaction be carried out at this elevated temperature, which is higher than the usual enzyme reaction temperature. If a crude enzyme preparation or a preparation containing intact cells is used, extraneous enzymes contained in the crude preparations may catalyze undesirable alternation of the substrate and product. These undesirable enzymatic reactions are prevented by carrying out the reaction at an elevated temperature, a useful advantage since even supposedly purified enzyme preparations may be contaminated with interferring enzymes. Such temperature control and elimination of competing pathways of reaction was not possible using previously known fermantation processes, which used live microorganisms. The ability to eliminate competing reactions by temperature control is an unexpected advantage of the present invention.

The 1-β-D-ribofuranosyl-1,2,4-triazole of formula (I) formed in the reaction mixture may be recovered by any conventional recovering method, such as crystallization, ion-exchange chromotography, or gel-filtration. Such separations are within the ability of those of ordinary skill in the art.

The above disclosure generally describes the present invention. A more complete understanding of the invention can be obtained by reference to the following specific examples, which are provided herein for purposes of illustration only and are not intended to be limiting unless otherwise specified.

EXAMPLE 1

Five ml portions of an aqueous medium, pH 7.0, which contain, per deciliter, 0.5 g yeast extract, 1.0 g peptone, 0.5 bouillon, and 0.5 g NaCl were poured into large test tubes and heated for sterilization.

One loopful inoculum of each of the microorganisms listed in Table 1 below was transferred into each batch of the culture medium, and cultivation was carried out at 30° C. for 24 hours with shaking. The microbial cells which accumulated in the culture broth were collected by centrifugation and washed with physiological saline. The cells were then suspended in 0.05M phosphate buffer, pH 7.0, to give cells suspensions containing 50 mg wet cells per milliliter.

Then, 0.5 ml of each cell suspension was mixed with 0.5 ml an aqueous solution of pH 7.0 containing, per milliliter, 20 mg uridine (or inosine), 2 mg 1,2,4-triazole-3-carboxamide, and 80 mg $KH_2PO_4$. The reaction mixture was maintained at 60° C. for 10 hours with occasional stirring and thereafter heated at 100° C. for 5 minutes.

All products formed in the solutions were identified to be virazole, i.e., 1-β-D-ribofuranosyl-1,2,4-triazole-3-carboxamide. The amount in each sample was determined by high pressure liquid chromatography (Model 635 of Hitachi Seisakusho, Tokyo).

The results obtained are shown in Table 1.

TABLE 1

| Test strain | Amount of virazole (mg/dl) formed when the ribofuranosyl donor was | |
|---|---|---|
| | Uridine | Inosine |
| ATCC 11568 | 15 | 10 |
| CCM 298 | 20 | 15 |
| CCM 69 | 25 | 32 |
| ATCC 8759 | 30 | 15 |
| ATCC 14536 | 55 | 20 |
| ATCC 9760 | 48 | 18 |
| ATCC 8090 | 70 | 15 |
| ATCC 4279 | 5 | 5 |
| ATCC 10798 | 15 | 15 |
| ATCC 13047 | 35 | 35 |
| IFO 3049 | 15 | 5 |
| ATCC 9621 | 50 | 20 |
| ATCC 398 | 20 | 25 |
| ATCC 7429 | 10 | 5 |
| ATCC 8185 | 30 | 25 |
| ATCC 8183 | 30 | 5 |
| ATCC 8010 | 25 | 10 |
| ATCC 6871 | 15 | 15 |
| ATCC 13270 | 5 | 5 |
| ATCC 6473 | 10 | 10 |
| ATCC 14174 | 25 | 25 |
| ATCC 2601 | 15 | 5 |
| ATCC 14056 | 10 | 5 |
| ATCC 155 | 32 | 10 |
| ATCC 6900 | 5 | 5 |

TABLE 1-continued

| Test strain | Amount of virazole (mg/dl) formed when the ribofuranosyl donor was | |
|---|---|---|
| | Uridine | Inosine |
| ATCC 7708 | 15 | 5 |

EXAMPLE 2

Each test strain listed in Table 2 was cultured in a manner similar to that described in Example 1. Cells in each sample were harvested by centrigugation, followed by washing with water serveral times. Cells suspension were adjusted to contain 50 mg wet cells per milliliter. The cell suspensions were then subjected to sonication for 5 minutes, with cooling, to rupture the cells. One-half ml of each suspension thus treated was mixed with 0.5 ml of an aqueous solution containing, per milliliter, 20 mg ribose-1-phosphate, 2 mg 1,2,4-triazole-3-carboxamide, and 8 mg $KH_2PO_4$. Then the mixture was kept at 60° C. for 10 hours followed by heating at 100° C. for 5 minutes.

Each product was identified as virazole, and the amount was determined in a manner similar to that described in Example 1. The results obtained are shown in Table 2.

TABLE 2

| Test strain | Amount virazole formed (mg/dl) |
|---|---|
| ATCC 11563 | 33 |
| CCM 298 | 42 |
| CCM 69 | 83 |
| ATCC 8759 | 88 |
| ATCC 14536 | 105 |
| ATCC 9760 | 93 |
| ATCC 8090 | 75 |
| ATCC 4278 | 18 |
| ATCC 13047 | 100 |
| IFO 3049 | 25 |
| ATCC 9621 | 115 |
| ATCC 9341 | 39 |
| ATCC 13060 | 16 |
| ATCC 6633 | 82 |
| ATCC 8183 | 75 |
| ATCC 8010 | 38 |
| ATCC 6871 | 45 |
| ATCC 15173 | 5 |
| ATCC 6473 | 16 |
| ATCC 14174 | 93 |
| ATCC 2601 | 25 |
| ATCC 14056 | 5 |

EXAMPLE 3

One hundred milliliters of an aqueous culture medium of pH 7.2 containing, per deciliter, 0.5 g yeast extract, 1.0 g peptone, 1.0 g bouillon, and 0.5 g NaCl were placed into a 500 ml flask and heated for sterilization. The flask was then inoculated with a seed culture of *Erwinia herbicola* ATCC 14536 and cultured with shaking at 30° C. for 63 hours.

5.0 g wet cells harvested from the culture broth by centrifugation were washed with 10 mM phosphate buffer, pH 7.0, and suspended into 10 ml of the same buffer to give 15 ml of cell suspension. The enzyme activities of uridine phosphorylase and purine phosphorylase in the suspension were 3.2 and 1.98 units per milliliter, respectively.

The cell suspension was then subjected to sonication for 15 minutes to rupture the cells. Ten ml of supernatant liquid obtained from the cell suspension thus treated were mixed with 90 ml of an aqueous solution of pH 7.0 containing 100 mg 1,2,4-triazole-3-carboxamide, 500 mg uridine, and 350 mg KH$_2$PO$_4$. The mixture was allowed to stand at 60° C. for 10 hours and thereafter heated at 100° C. for 5 minutes. The product formed in the solution was identified as virazole by high pressure liquid chromatography. The solution was then centrifuged to remove insoluble materials and concentrated. The concentrated solution was applied to an Sephadex G-100 column and eluted with water.

The combined fractions containing virazole were cooled to a low enough temperature to crystallize virazole and kept overnight to conclude the crystallization. The crystals thus obtained were recrystallized from water, and 135 mg of purified crystals were obtained. The crystalline product was also identified as virazole based on its NMR spectrum, IR spectrum, and UV spectrum.

EXAMPLE 4

Klebsiella pneumoniae ATCC 9621 was cultured in a manner similar to that described in Example 1. Microbial cells were harvested and washed with water. Then 5.0 g wet cells were incubated with 2.0 g/dl ribose-1-phosphate (or 2.0 g/dl uridine and 8 g KH$_2$PO$_4$) and 0.2 g/dl 1,2,4-triazole-3-carboxamide in 0.1M tris buffer of pH 7.0 at various temperature ranging from 20° to 80° C. for 5 hours. The amount of virazole in each solution was determined in a manner similar to that described in Example 1, and the results obtained are shown in Table 3.

TABLE 3

| Temperature | Amount of virazole (mg/dl) produced when ribofuranosyl donor was | |
|---|---|---|
| | Ribose-1-P | Uridine |
| 20 | 18 | 8 |
| 25 | 23 | 15 |
| 30 | 35 | 18 |
| 35 | 45 | 25 |
| 40 | 60 | 32 |
| 45 | 85 | 35 |
| 50 | 90 | 40 |
| 55 | 95 | 48 |
| 60 | 105 | 50 |
| 65 | 90 | 45 |
| 70 | 23 | 15 |
| 75 | 0 | 0 |
| 80 | 0 | 0 |

EXAMPLE 5

Corynebacterium michiganense ATCC 7429 was cultured in a manner similar to that described in Example 3. Microbial cells were harvested and washed with water. Then 50 mg wet cells were mixed with 1.0 ml of 10 mM Tris buffer at pH 7.0 containing 20 mg of a 1,2,4-triazole having a formula as shown in Table 4 and 10 mg ribose-1-phosphate. Then the mixture was kept at 60° C. for 10 hours, followed by heating at 100° C. for 5 minutes.

Each product formed in each reaction solution was identified, and the amount was determined in a manner similar to that described in Example 1. The results obtained are shown in Table 4.

TABLE 4

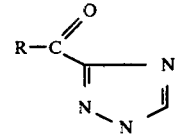

| R | Product formed | amount |
|---|---|---|
| OH group | 1-β-D-Ribofuranosyl-1,2,4-triazole-3-carboxylic acid | 20 mg/dl |
| NH$_2$ group | 1-β-D-Ribofuranosyl-1,2,4-triazole-3-carboxamide | 650 mg/dl |
| OCH$_3$ | 1-β-D-Ribofuranosyl-1,2,-4 triazole-3-carboxymethyl ester | 10 mg/dl |

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing a 1-β-D-ribofuranosyl-1,2,4-triazole of the formula:

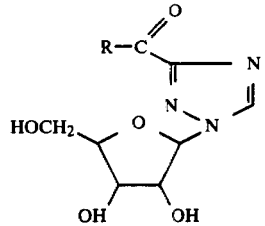

wherein R is hydroxy, amino, or alkoxy, which comprises:

reacting a 1,2,4 triazole of the formula:

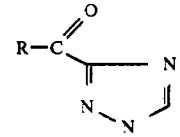

wherein R is hydroxy, amino, or alkoxy, with a greater than equimolar amount of a ribofuranosyl group donor selected from the group consisting of ribose-1-phosphate, purine nucleosides, purine nucleotides, pyrimidine nucleosides, and pyrimidine nucleotides in the presence of a nucleoside phosphorylase preparation at a temperature in the range from 55° to 65° C. for a period from 10 minutes, to 20 hours, and recovering said 1-β-ribofuranosyl-1,2,4-triazole from the reaction mixture.

2. The method of claim 1, wherein said 1-β-D-ribofuranosyl-1,2,4-triazole is 1-β-D-ribofuranosyl-1,2,4-triazole-3-carboxamide.

3. The method of claim 1, wherein said ribofuranosyl group donor is selected from the group consisting of adenosine, guanosine, xanthosine, inosine, uridine, thymidine, cytosine, adenylic acid, guanidylic acid, inosinic acid, uridylic acid and cytidylic acid.

4. The method of claim 1, wherein said nucleoside phosphorylase preparation is obtained from a microorganism belonging to a genera selected from the group consisting of Pseudomonas, Flavobacterium, Achromobacter, Salmonella, Erwinia, Bacterium, Xanthomonas, Citrobacter, Mycollana, Escherichia, Enterobacter, Klebsiella, Micrococcus, Bacillus, Arthrobacter, Brevibacterium, Sporosarcina, Aeromonus, and Staphylococcus.

* * * * *